(12) United States Patent
Khosravi et al.

(10) Patent No.: US 7,331,979 B2
(45) Date of Patent: Feb. 19, 2008

(54) APPARATUS AND METHODS FOR SEALING A VASCULAR PUNCTURE

(75) Inventors: Farhad Khosravi, San Mateo, CA (US); Celso J. Bagaoisan, Union City, CA (US); Stephen Ramee, New Orleans, LA (US)

(73) Assignee: Access Closure, Inc., Mountain View, CA (US)

( * ) Notice: Subject to any disclaimer, the term of this patent is extended or adjusted under 35 U.S.C. 154(b) by 1150 days.

(21) Appl. No.: 10/454,362

(22) Filed: Jun. 4, 2003

(65) Prior Publication Data
US 2004/0249342 A1  Dec. 9, 2004

(51) Int. Cl.
*A61B 17/08* (2006.01)
(52) U.S. Cl. .................................... 606/213
(58) Field of Classification Search ............... 606/213, 606/214, 216, 139, 142, 143, 222, 232, 233
See application file for complete search history.

(56) References Cited

U.S. PATENT DOCUMENTS

| | | | |
|---|---|---|---|
| 2,115,492 | A | 4/1938 | Kober |
| 3,765,419 | A | 10/1973 | Usher |
| 4,260,077 | A | 4/1981 | Schroeder |
| 4,327,709 | A | 5/1982 | Hanson et al. |
| 4,362,150 | A | 12/1982 | Lombardi, Jr. et al. |
| 4,540,404 | A | 9/1985 | Wolvek |
| 4,598,707 | A | 7/1986 | Agdanowski et al. |
| 4,655,211 | A | 4/1987 | Sakamoto et al. |
| 4,738,658 | A | 4/1988 | Magro et al. |
| 4,838,280 | A | 6/1989 | Haaga |
| 4,838,864 | A | 6/1989 | Peterson |
| 4,852,568 | A | 8/1989 | Kensey |

(Continued)

FOREIGN PATENT DOCUMENTS

EP    0 476 178 A1    3/1992

(Continued)

OTHER PUBLICATIONS

PCT International Search Report for PCT/US2006/014562, Applicant: AccessClosure, Inc., Forms PCT/ISA/210 and PCT/ISA/220, dated Aug. 12, 2006, 8 pages.

(Continued)

*Primary Examiner*—Kevin T. Truong
(74) *Attorney, Agent, or Firm*—William A. English; Vista IP Law Group LLP

(57) ABSTRACT

An apparatus for sealing a puncture communicating with a blood vessel includes an inner member slidable within an outer member, and a balloon coupled to distal ends of the inner and outer members. A proximal end of the outer member includes a port for delivering fluid into the balloon, and a cylinder that communicates with the port. A piston coupled to the inner member is slidable and biased to move distally within the cylinder. The apparatus is introduced into the puncture until the collapsed balloon is disposed within the vessel. Fluid is introduced into the port, moving the inner member proximally to shorten the balloon as it expands. The balloon is withdrawn to seal the puncture, and a hydrogel is introduced into the puncture. Fluid is removed via the port, moving the inner member distally to extend the balloon as it collapses, and the apparatus is withdrawn from the puncture.

21 Claims, 8 Drawing Sheets

U.S. PATENT DOCUMENTS

| | | |
|---|---|---|
| 4,890,612 A | 1/1990 | Kensey |
| 4,948,092 A | 8/1990 | Kasper et al. |
| 5,061,274 A | 10/1991 | Kensey |
| 5,085,249 A | 2/1992 | Dragan et al. |
| 5,104,375 A | 4/1992 | Wolf et al. |
| 5,104,389 A | 4/1992 | Deem et al. |
| 5,108,421 A | 4/1992 | Fowler |
| 5,192,300 A | 3/1993 | Fowler |
| 5,192,302 A | 3/1993 | Kensey et al. |
| 5,221,259 A | 6/1993 | Weldom et al. |
| 5,258,042 A | 11/1993 | Mehta |
| 5,259,835 A | 11/1993 | Clark et al. |
| 5,275,616 A | 1/1994 | Fowler |
| 5,290,310 A | 3/1994 | Makower et al. |
| 5,292,332 A | 3/1994 | Lee |
| 5,306,254 A | 4/1994 | Nash et al. |
| 5,320,639 A | 6/1994 | Rudnick |
| 5,324,306 A | 6/1994 | Makower et al. |
| 5,334,216 A | 8/1994 | Vidal |
| 5,383,896 A | 1/1995 | Gershony et al. |
| RE34,866 E | 2/1995 | Kensey et al. |
| 5,391,183 A | 2/1995 | Janzen et al. |
| 5,413,571 A | 5/1995 | Katsaros et al. |
| 5,419,765 A | 5/1995 | Weldon et al. |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,464,396 A | 11/1995 | Barta et al. |
| 5,486,195 A | 1/1996 | Myers et al. |
| 5,489,278 A | 2/1996 | Abrahamson |
| 5,514,158 A | 5/1996 | Kanesaka |
| 5,529,577 A | 6/1996 | Hammerslag |
| 5,550,187 A | 8/1996 | Rhee |
| 5,571,181 A | 11/1996 | Li |
| 5,580,923 A | 12/1996 | Yeung |
| 5,591,204 A | 1/1997 | Janzen et al. |
| 5,591,205 A | 1/1997 | Fowler |
| 5,601,602 A | 2/1997 | Fowler |
| 5,626,601 A | 5/1997 | Gershony et al. |
| 5,637,086 A | 6/1997 | Ferguson et al. |
| 5,643,464 A | 7/1997 | Rhee |
| 5,660,849 A | 8/1997 | Polson et al. |
| 5,716,375 A | 2/1998 | Fowler |
| 5,725,498 A | 3/1998 | Janzen et al. |
| 5,725,551 A | 3/1998 | Myers et al. |
| 5,728,122 A | 3/1998 | Leschinsky et al. |
| 5,731,368 A | 3/1998 | Stanley et al. |
| 5,741,223 A | 4/1998 | Janzen et al. |
| 5,744,153 A | 4/1998 | Yewey et al. |
| 5,752,974 A | 5/1998 | Rhee et al. |
| 5,780,044 A | 7/1998 | Yewey et al. |
| 5,782,860 A | 7/1998 | Epstein et al. |
| 5,785,679 A | 7/1998 | Abolfathi et al. |
| 5,795,331 A | 8/1998 | Cragg et al. |
| 5,814,016 A | 9/1998 | Valley et al. |
| 5,830,130 A | 11/1998 | Janzen et al. |
| 5,836,970 A | 11/1998 | Pandit |
| 5,843,124 A | 12/1998 | Hammerslag |
| 5,868,778 A | 2/1999 | Gershony |
| 5,916,236 A | 6/1999 | Muijs Van de Moer et al. |
| 5,922,009 A | 7/1999 | Epstein et al. |
| 5,928,266 A | 7/1999 | Kontos |
| 5,941,847 A | 8/1999 | Huber et al. |
| 5,951,583 A | 9/1999 | Jensen et al. |
| 5,951,589 A | 9/1999 | Epstein et al. |
| 5,957,952 A | 9/1999 | Gershony |
| 6,017,359 A | 1/2000 | Gershony et al. |
| 6,022,361 A | 2/2000 | Epstein et al. |
| 6,027,471 A | 2/2000 | Fallon et al. |
| 6,045,570 A | 4/2000 | Epstein et al. |
| 6,051,248 A | 4/2000 | Sawhney et al. |
| 6,056,768 A | 5/2000 | Cates |
| 6,056,769 A | 5/2000 | Epstein et al. |
| 6,083,522 A | 7/2000 | Chu |
| 6,152,943 A | 11/2000 | Sawhney |
| 6,162,240 A | 12/2000 | Cates |
| 6,162,241 A | 12/2000 | Coury et al. |
| 6,165,201 A | 12/2000 | Sawhney |
| 6,179,862 B1 | 1/2001 | Sawhney |
| 6,238,412 B1 | 5/2001 | Dubrul |
| 6,287,323 B1 | 9/2001 | Hammerslag |
| 6,296,658 B1 | 10/2001 | Gershony |
| 6,299,597 B1 | 10/2001 | Buscemi et al. |
| 6,302,898 B1 | 10/2001 | Edwards et al. |
| 6,325,789 B1 | 12/2001 | Janzen |
| 6,350,274 B1 | 2/2002 | Li |
| 6,368,300 B1 | 4/2002 | Fallon et al. |
| 6,371,975 B2 | 4/2002 | Cruise et al. |
| 6,379,373 B1 | 4/2002 | Sawhney |
| 6,458,147 B1 | 10/2002 | Cruise et al. |
| 6,475,177 B1 | 11/2002 | Suzuki |
| 6,514,534 B1 | 2/2003 | Sawhney |
| 6,562,059 B2 | 5/2003 | Edwards et al. |
| 6,566,406 B1 | 5/2003 | Pathak |
| 6,569,185 B2 | 5/2003 | Ungs |
| 6,605,294 B2 | 8/2003 | Sawhney |
| 6,613,070 B2 | 9/2003 | Redmond et al. |
| 6,626,861 B1 * | 9/2003 | Hart et al. ............ 604/96.01 |
| 6,626,918 B1 * | 9/2003 | Ginn et al. ............ 606/213 |
| 6,635,068 B1 | 10/2003 | Dubrul |
| 6,689,148 B2 | 2/2004 | Sawhney |
| 6,703,047 B2 | 3/2004 | Sawhney |
| 6,818,008 B1 | 11/2004 | Cates |
| 6,818,018 B1 | 11/2004 | Sawhney |
| 6,887,974 B2 | 5/2005 | Pathak |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney |
| 2002/0111392 A1 | 8/2002 | Cruise |
| 2002/0111651 A1 | 8/2002 | Ungs |
| 2002/0188319 A1 | 12/2002 | Morris et al. |
| 2003/0008831 A1 | 1/2003 | Yang et al. |
| 2003/0051735 A1 | 3/2003 | Pavcnik |
| 2003/0088269 A1 | 5/2003 | Ashby |
| 2003/0088271 A1 | 5/2003 | Cragg et al. |
| 2003/0135234 A1 | 7/2003 | Fisher et al. |
| 2003/0135235 A1 | 7/2003 | Fisher et al. |
| 2003/0135236 A1 | 7/2003 | Fisher et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |
| 2003/0233120 A1 | 12/2003 | Akerfeldt |
| 2004/0122350 A1 | 6/2004 | Zhong |
| 2004/0249342 A1 | 12/2004 | Khosravi et al. |

FOREIGN PATENT DOCUMENTS

| | | |
|---|---|---|
| EP | 0 482 350 B1 | 4/1992 |
| WO | WO 92/22252 | 12/1992 |
| WO | 9533510 | 12/1995 |
| WO | WO 00/19912 | 4/2001 |

| | | |
|---|---|---|
| WO | WO 03/094749 | 11/2003 |

OTHER PUBLICATIONS

PCT Written Opinion for PCT/US2006/014562, Applicant: AccessClosure, Inc., Forms PCT/ISA/237, dated Aug. 12, 2006, 8 pages.

PCT International Search Report for PCT/US2004/016938, Applicant: AccessClossure, Inc., Forms PCT/ISA/210 and 220, dated Mar. 2, 2005 (7 pages).

PCT Written Opinion of the International Search Authority for PCT/US2004/016938, Applicant: AccessClossure, Inc., Form PCT/ISA/237, dated Mar. 2, 2005 (9 pages).

PCT Partial International Search Report for PCT/US2004/016938, Applicant: AccessClossure, Inc., Forms PCT/ISA/206, dated Nov. 12, 2004 (6 pages).

* cited by examiner

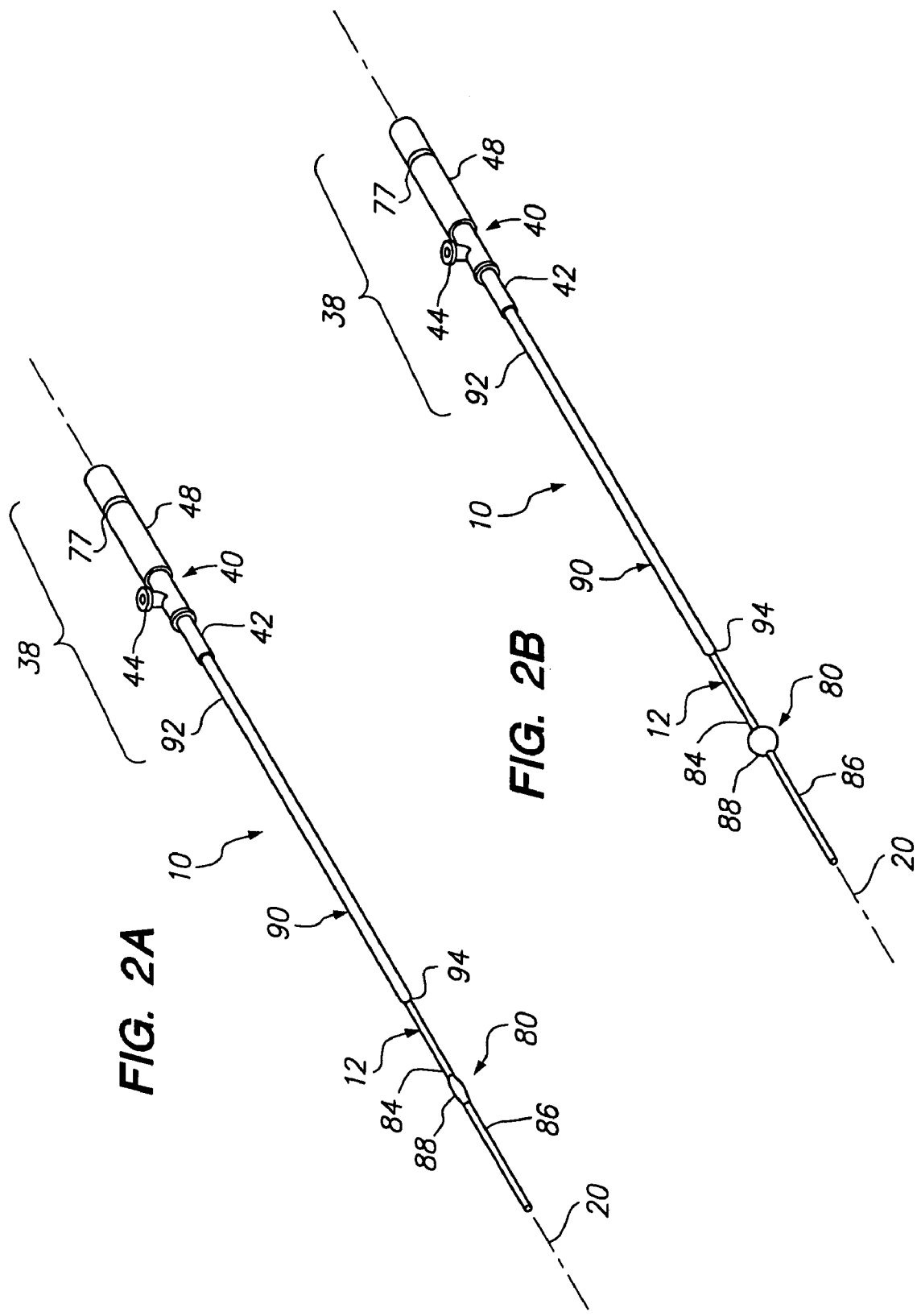

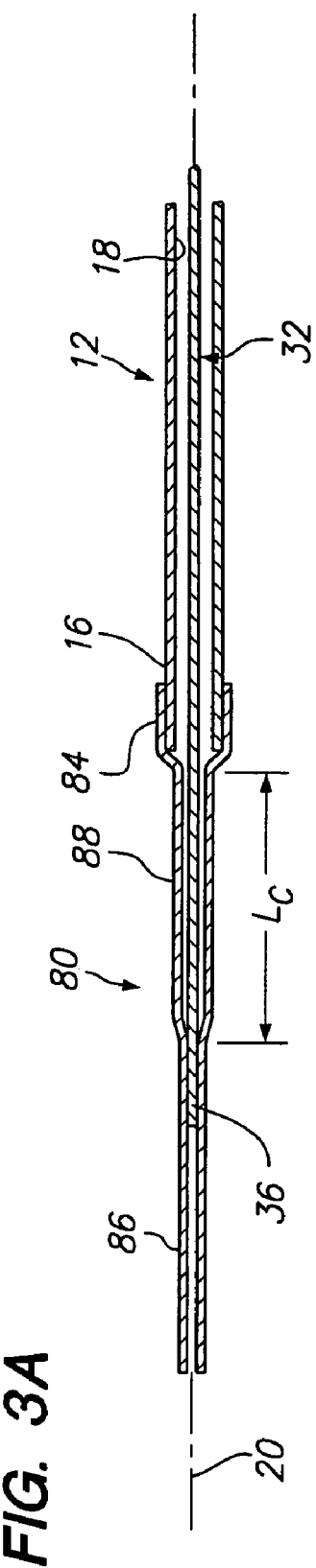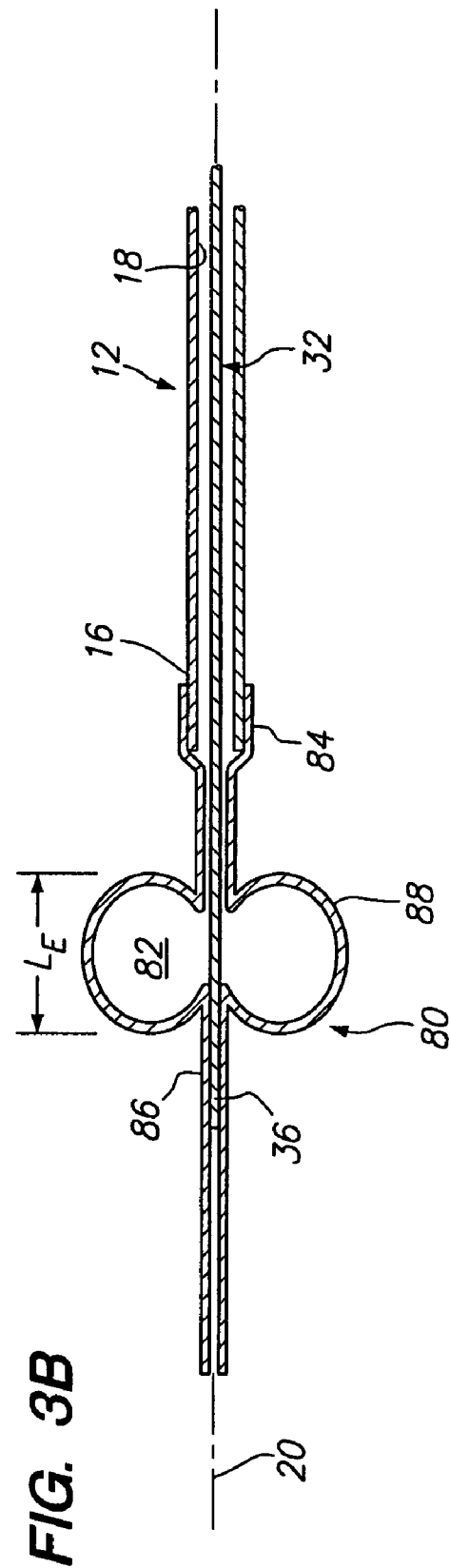

APPARATUS AND METHODS FOR SEALING A VASCULAR PUNCTURE

FIELD OF THE INVENTION

The present invention relates generally to apparatus and methods for sealing punctures in a body, and more particularly, to apparatus and methods for sealing a vascular puncture extending through tissue into a blood vessel and to apparatus and methods for delivering a sealing compound into a percutaneous puncture extending from a patient's skin to a blood vessel or other body lumen to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a collagen plug that may be delivered into a puncture through tissue. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon, thereby preventing the plug from entering the vessel. Once the plug is positioned within the puncture, the balloon may be deflated and withdrawn, leaving the plug therein to expand and seal the puncture and/or to promote hemostasis.

Alternatively, U.S. Pat. Nos. 5,192,302 and 5,222,974 issued to Kensey et al. describe a biodegradable collagen plug that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism.

Accordingly, apparatus and methods for sealing punctures, e.g., a percutaneous puncture communicating with a blood vessel, would be useful.

SUMMARY OF THE INVENTION

The present invention is directed to apparatus and methods for sealing a puncture in a body, and, more particularly, to apparatus and methods for providing temporary or permanent hemostasis within a vascular puncture extending into a blood vessel and/or to apparatus and methods for delivering a sealing compound into a percutaneous puncture extending from a patient's skin to a blood vessel or other body lumen.

In accordance with one aspect of the present invention, an apparatus is provided for sealing a puncture through tissue that includes an outer member, an inner member slidably coupled to the outer member, and a balloon or other expandable member coupled to distal ends of the inner and outer members.

In one embodiment, the outer member may include proximal and distal ends defining a longitudinal axis therebetween, and a lumen extending between the proximal and distal ends. The expandable member may include proximal and distal ends, the proximal end of the expandable member being coupled to the distal end of the outer member such that an interior of the expandable member communicates with the lumen. Thus, the expandable member may be expandable from a collapsed state to an expanded state when fluid is introduced into the lumen of the outer member, and consequently into the interior of the expandable member.

The inner member may include proximal and distal ends, the distal end being coupled to the distal end of the expandable member. Preferably, the inner member is slidably disposed within the lumen of the outer member for moving the distal end of the expandable member towards or away from the proximal end of the expandable member. An element, e.g., a piston, may be coupled to the inner member that includes a surface exposed to the lumen such that, when fluid is introduced into the lumen, fluid pressure from the fluid may push against the surface, causing the inner member to move proximally relative to the outer member. Because the distal end of the inner member is coupled to the distal end of the balloon, this proximal movement of the inner member may move the distal end of the expandable member towards the proximal end of the expandable member, thereby shortening the expandable member as it expands.

For example, the outer member may include a port on the proximal end that communicates with the lumen, i.e., for connecting a source of fluid to the lumen. A cylinder may extend from the proximal end of the outer member, and the piston may be slidable within the cylinder. The piston may divide the cylinder into proximal and distal chambers, the distal chamber communicating with the lumen. In one embodiment, a biasing mechanism, e.g., a spring, pressurized fluid, and/or other expandable/compressible materials, may be provided in the proximal chamber for pushing the piston distally relative to the cylinder, thereby biasing the inner member distally relative to the outer member. Alternatively, the piston may be free floating within the cylinder such that a pressure differential within the lumen (as fluid is delivered into or evacuated from the lumen) may cause the piston to slide distally or proximally within the cylinder.

Thus, the expandable member may have a length that may shorten as the expandable member is expanded, i.e., as fluid is delivered into the lumen, and that may lengthen as the expandable member is collapsed, i.e., as fluid is withdrawn from the lumen. In one embodiment, the expandable member may at least partially evert, i.e., the proximal and distal ends may partially enter the interior of the expandable member as it expands towards the expanded state.

Optionally, the apparatus may include an elongate tubular member, e.g., an introducer sheath, including proximal and distal ends, and a lumen extending therebetween. Preferably, the lumen has sufficient size for receiving the outer member therein when the expandable member is in the collapsed state. In addition, a source of sealing compound may be provided that may be coupled to the proximal end of the tubular member for delivering a sealing compound into the lumen between the sheath and the outer member. In a preferred embodiment, the source of sealing compound includes multiple chambers including polymers that may be mixed and/or otherwise injected into the tubular member to create a hydrogel within a tissue space.

In accordance with another aspect of the present invention, a method is provided for sealing a puncture extending through tissue and/or communicating with a body lumen using an apparatus including an outer member, an inner member slidably coupled to the outer member, and an expandable member coupled to distal ends of the inner and outer members. For example, the body lumen may be a blood vessel, e.g., a femoral, carotid, or other peripheral artery.

The apparatus may be introduced into the puncture with the expandable member in a collapsed state until the expandable member is disposed within the body lumen. For example, the apparatus may be introduced through a lumen of an introducer sheath or other tubular member previously placed in the puncture. Fluid may be introduced into the outer member to expand the expandable member to an expanded state, the fluid causing the inner member to move proximally relative to the outer member to shorten the length of the expandable member as it expands.

The apparatus may be at least partially withdrawn from the puncture until the expandable member engages a location where the puncture penetrates a wall of the body lumen, thereby substantially sealing the puncture from the body lumen. Optionally, a sealing material, e.g., a multiple component liquid sealing compound, may be introduced into the puncture around the outer member.

Fluid may be removed from the expandable member through the outer member, thereby collapsing the expandable member to the collapsed state and causing the inner member to move distally relative to the outer member to extend the length of the expandable member. The apparatus may be withdrawn from the puncture, e.g., through the sealing material with the expandable member in the collapsed state. Preferably, the sealing material is a liquid compound, and the apparatus may be withdrawn only after sufficient time for the liquid sealing compound to at least partially solidify, e.g., to create a hydrogel.

If desired, pressure may be applied to skin overlying the body lumen, e.g., to at least partially suppress fluid flow through the body lumen as the apparatus is withdrawn from the puncture.

In one embodiment, an introducer sheath may be introduced through the puncture into the body lumen, and the apparatus may be introduced into the puncture through the introducer sheath. The sealing material may be introduced into the puncture through the introducer sheath, e.g., between the outer member and the sheath. Preferably, the introducer sheath may be withdrawn from the puncture as the sealing compound is introduced into the puncture, e.g., to substantially fill the puncture with the sealing compound.

In accordance with yet another aspect of the present invention, an apparatus is provided for sealing a puncture or other tract through tissue communicating with a body lumen. Generally, the apparatus includes a source of sealing material that includes a plurality of chambers including polymer components that create a hydrogel when mixed together, an outer sleeve or sheath insertable into a tract through tissue, and a balloon catheter insertable into the outer sleeve or sheath.

The outer sleeve or sheath may include one or more lumens extending between its proximal and distal ends, and one or more ports communicating with the one or more lumens. One or more conduits, e.g., flexible tubing may connect the plurality of chambers with the one or more lumens, e.g., via the one or more ports. In a preferred embodiment, the outer sleeve or sheath may include a single lumen, and the one or more conduits may include a "Y" fitting for mixing the polymer components in the chambers together before being delivered into the lumen of the outer sleeve or sheath.

The catheter may include an outer member, an inner member slidably coupled to the outer member, and an expandable member coupled to distal ends of the inner and outer members. The catheter may be insertable through the lumen of the outer sleeve or sheath when the expandable member is collapsed. In one embodiment, the outer member may include a lumen extending between its proximal and distal ends, and the inner member may be slidably disposed in the lumen for moving a distal end of the expandable member towards or away from a proximal end of the expandable member.

An element, e.g., a piston, may be coupled to the inner member that includes a surface exposed to the lumen such that, when fluid is introduced into the lumen, fluid pressure from the fluid may push against the surface, causing the inner member to move proximally. This causes the distal end of the expandable member to move towards the proximal end of the expandable member, thereby shortening the expandable member as it expands. Conversely, when the fluid is evacuated to collapse the expandable member, the inner member may move distally, thereby lengthening the expandable member as it is collapsed.

In accordance with still another aspect of the present invention, a method is provided for sealing a tract through tissue communicating with a blood vessel, such as a femoral artery. An introducer sheath or other tubular member may be introduced into the tract, e.g., in order to provide access to the vessel. An elongate member with an expandable member thereon may be inserted through the sheath with the expandable member in a collapsed state until the expandable member is disposed within the body lumen.

Fluid may be introduced through the elongate member to expand the expandable member to an expanded state, the fluid causing the expandable member to shorten as it expands. The apparatus may be at least partially withdrawn from the tract until the expandable member engages a location where the tract penetrates a wall of the vessel, thereby substantially sealing the tract from the vessel. Polymer components may be introduced into the tract through the tubular member to create a hydrogel within the tract.

Fluid may be removed from the expandable member, thereby collapsing the expandable member to the collapsed state and causing the expandable member to extend distally as it collapses. With the expandable member in the collapsed state, the elongate member may be withdrawn from the tract, e.g., through the hydrogel after the hydrogel has at least partially solidified. Optionally, the introducer sheath may be withdrawn from the tract as the polymer components are introduced into the tract, e.g., to substantially fill the tract with the hydrogel.

Other objects and features of the present invention will become apparent from consideration of the following description taken in conjunction with the accompanying drawings.

BRIEF DESCRIPTION OF THE DRAWINGS

FIGS. 2A and 2B are perspective views of the apparatus of FIG. 1, showing a balloon thereon in collapsed and expanded states, respectively.

FIGS. 3A and 3B are cross-sectional details of a distal portion of the apparatus shown in FIGS. 2A and 2B, respectively.

DETAILED DESCRIPTION OF THE PREFERRED EMBODIMENTS

Figure 1:
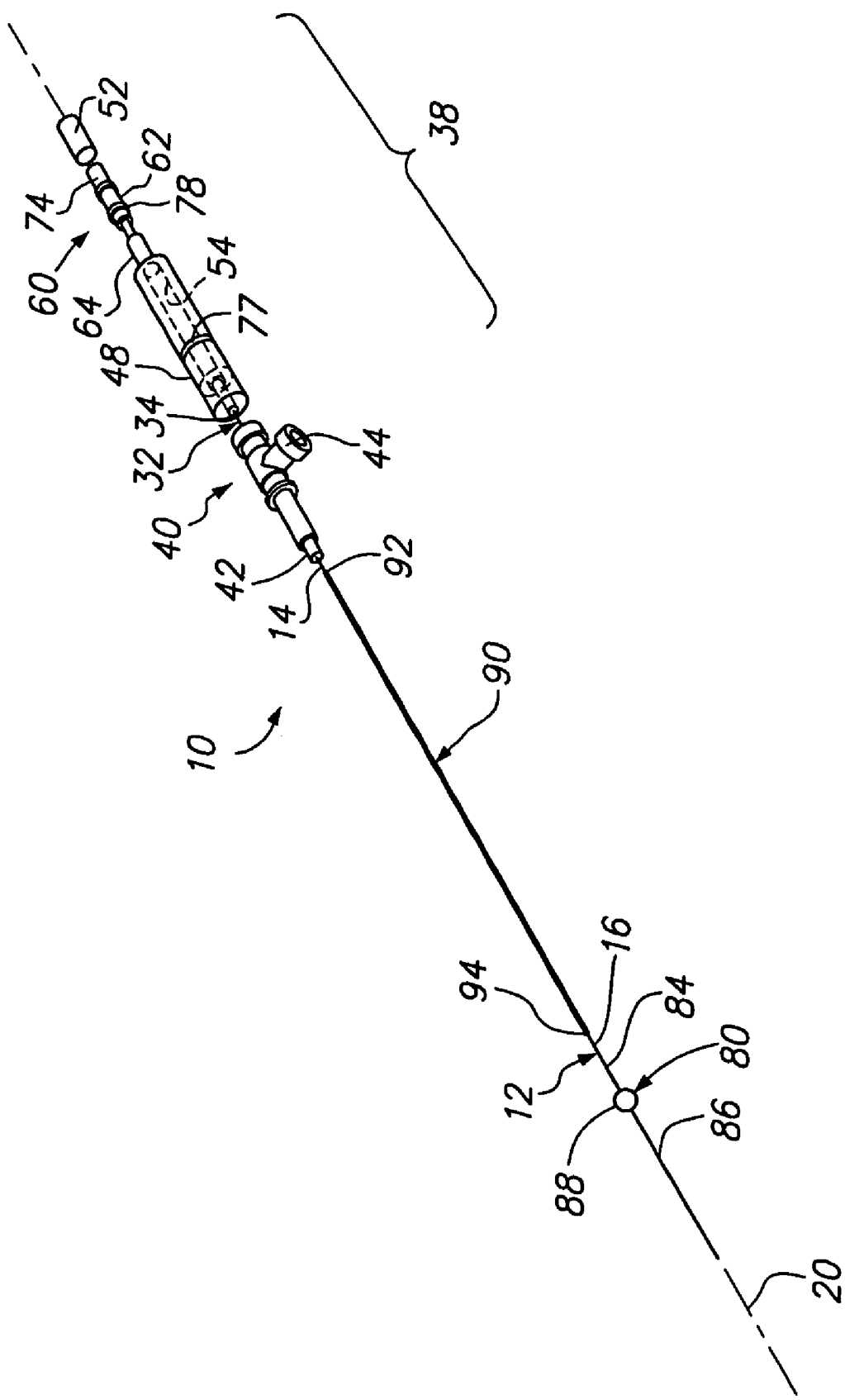
FIG. 1 is an exploded perspective view of a preferred embodiment of an apparatus for sealing a puncture through tissue, in accordance with the present invention.

Turning to the drawings, FIGS. 1-6 show a preferred embodiment of an apparatus 10 for sealing a puncture extending through tissue and/or communicating with a body lumen (not shown). Generally, the apparatus 10 includes an outer member 12, an inner member 32 slidably coupled to the outer member 12 (best seen in FIGS. 3A, 3B, and 5), a hub subassembly 38 or other mechanism for biasing the inner member 32 relative to the outer member 12, and a balloon or other expandable member 80 coupled to the inner and outer members 32, 12. Optionally, the apparatus 10 may include an outer sleeve 90 that may at least partially cover the outer member 12.

With particular reference to FIGS. 1, 3A, and 3B, the outer member 12 may be an elongate tubular body including a proximal end 14, a distal end 16, and a lumen 18 extending therebetween (shown in FIGS. 3A, 3B, and 5), thereby defining a longitudinal axis 20. The outer member 12 may be flexible, semi-rigid, or rigid, e.g., having a uniform or variable flexibility along its length. The outer member 12 may be formed from a variety of materials providing a desired rigidity, e.g., plastic, such as polyamide, PEEK, nylon, PET, PEBAX, polyethylene, and/or metal, such as stainless steel or a nickel-titanium alloy, fabricated using known processes, e.g., extrusion, roll forming, machining, and the like. Optionally, a lubricious coating (not shown) may be provided on the exterior of the outer member 12, e.g., Dow 360 silicone fluid.

Preferably, the distal end 16 is substantially flexible such that the distal end 16 may curve, bend, or otherwise conform substantially to the contour of a puncture and/or body lumen (not shown) into which the distal end 16 is advanced. The distal end 16 of the outer member 12 may have a size sufficient to be inserted into a relatively small puncture and/or body lumen. For example, the distal end 16 (and possibly the remainder of the outer member 12) may have an outer diameter between about 0.010-0.030 inch (0.25-0.75 mm), and preferably less than about 0.020 inch (0.5 mm).

An outer sleeve 90 may be provided that at least partially surrounds the outer member 12. Exemplary materials for the outer sleeve 90 may include plastics, such as polyamide, PEEK, nylon, PET, PEBAX, and polyethylene, metals, such as stainless steel, and nickel titanium, and/or composite materials. The outer sleeve 90 may include a proximal end 92 connected to the hub subassembly 38 and a tapered distal end 94 that terminates proximal to the distal end 16 of the outer member 12, as best seen in FIGS. 1, 2A, and 2B. For example, the proximal end 90 and the hub subassembly 38 may include cooperating connectors, e.g., luer lock connectors (not shown), for detachably connecting the outer sleeve 90 to the hub subassembly 38. Alternatively, the proximal end 92 of the outer sleeve 90 may be substantially permanently attached to the hub subassembly 38, e.g., using an adhesive, mating threads, an interference fit, and the like.

The outer sleeve 90 may enhance a rigidity and/or pushability of the outer member 12, i.e., may be sufficiently rigid to support the outer member 12, e.g., to prevent the outer member 12 from buckling or kinking when being advanced into a puncture (not shown). In addition, as explained below, where a sealing material is delivered around the outer sleeve 90 into a puncture (e.g., through an introducer sheath, not shown), the outer sleeve 90 may significantly reduce a volume that must be filled in order to deliver sealing material beyond the introducer sheath (as opposed to delivering the sealing material through the introducer sheath outside the outer member 12. This may reduce the cost of expensive sealing materials, such as hydrogel polymers, that may remain within the introducer sheath after the sealing material has been delivered, e.g., if the introducer sheath is not removed from the puncture. If the introducer sheath is removed from the puncture as the sealing material is delivered, the outer sleeve 90 may also minimize a thickness of the hydrogel around the outer sleeve 90 as the introducer sheath is pulled back (e.g., when the tip of the introducer sheath is located over the outer sleeve 90). This may also allow the formed hydrogel to break off more easily around the tip of the introducer sheath, because the hydrogel thickness is the thinnest e.g. weakest, preventing disruption of the formed hydrogel within the remainder of the puncture.

In addition, the outer sleeve 90 may be used to exchange one apparatus 10 for another, e.g., in the event that the balloon 80 ruptures or if a different size balloon 80 is desired. Furthermore, the outer sleeve 90 may include a side port (not shown) on the proximal end 92 for delivering a fluid, e.g., a liquid sealing compound between the outer sleeve 90 and the outer member 12, as explained further below.

With continued reference to FIGS. 1, 3A, and 3B, the inner member 32 may be an elongate body including a proximal end 34 (shown in FIGS. 1 and 6), and a distal end 36. Preferably, as best seen in FIGS. 3A and 3B, the inner member 32 is slidably received within the lumen 18 of the outer member 12 such that the distal end 36 of the inner member 32 extends beyond the distal end 16 of the outer member 12. More preferably, the inner member 32 is sufficiently small such that the inner member 32 may be received in the lumen 18 of the outer member 12, yet accommodate fluid being delivered through the lumen 18, i.e., along an exterior of the inner member 32.

When the inner member 32 is disposed within the lumen 18, the distal end 36 of the inner member 32 may extend substantially beyond the distal end 16 of the outer member 12. Preferably, the distal end 34 of the inner member 32 is attached to the balloon 80, as explained further below. Alternatively, the distal end 36 of the inner member 32 may terminate in a substantially flexible and/or atraumatic distal tip, e.g., a "J" tip and the like (not shown).

The inner member 32 may be a solid or hollow wire, hypotube, catheter, and the like, formed from a variety of materials, e.g., plastic and/or metal, similar to the outer member 12. For example, the inner member 32 may be a solid nickel-titanium alloy ("Nitinol"), stainless steel, polymeric and/or composite wire having an outer diameter between about 0.003-0.020 inch (0.075-0.5 mm), and preferably less than about 0.010 inch (0.25 mm). Optionally, the inner member 32 may include a lumen (not shown) for receiving a guidewire (not shown) therethrough, e.g., such that the apparatus 10 may be advanced over a guidewire.

Preferably, the inner member 32 is biased to move distally relative to the outer member 12, i.e., from a proximal position (such as that shown in FIG. 3B) to a distal position (such as that shown in FIG. 3A), e.g., to facilitate collapsing the balloon 80, as explained further below.

Figure 4:
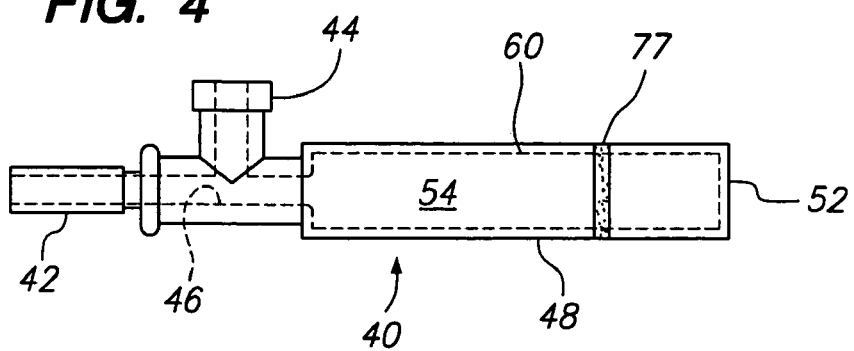
FIG. 4 is a side view of a housing for a hub subassembly of the apparatus of FIG. 1.

Turning to FIGS. 1 and 4-6, the hub subassembly 38 may be provided for biasing the inner member 32 relative to the outer member 12. Generally, the hub subassembly 38 includes a housing 40 extending from the proximal end 14 of the outer member 12 and a piston 60 coupled to the proximal end 34 of the inner member 32. As best seen in FIG. 4, the housing 40 includes a hollow adaptor end 42, a side port 44 communicating with an interior 46 of the housing 40, and a hollow cylinder 48. The cylinder 48 may include an outer wall 50 and a proximal end wall 52, thereby defining a chamber 54 that communicates with the interior 46 of the housing 40. The end wall 52 may only partially enclose the chamber 54 or may substantially seal the chamber 54, as explained further below.

The adapter end 42 of the housing 40 may be attached to the proximal end 14 of the outer member 12 such that the interior 46 of the housing 40 communicates with the lumen 18 of the outer member 12. For example, the adapter end 42 may be attached to the proximal end 14 of the outer member 12 using an adhesive, an interference fit, mating threads, and the like, e.g., to substantially permanently attach the housing 40 to the proximal end 14 of the outer member 12. With the housing 40 attached to the outer member 12, the side port 44 may communicate with the lumen 18 via the interior 46. Thus, fluid delivered into the side port 44 may enter the lumen 18 as well as the chamber 54 of the cylinder 48 via the interior 46 of the housing 40.

The side port 44 may include a connector, e.g., a luer lock connector, or a nipple (not shown) for connecting tubing or otherwise connecting a source of fluid (not shown) to the side port 44. For example, as shown in FIGS. 7C and 7F, a syringe 160 filled with inflation media, e.g., saline, carbon dioxide, and the like, may be connected to the side port 44 for manually delivering the inflation media into the lumen 18. Alternatively, a pump or other device (not shown) may be provided for delivering fluid at a desired pressure and/or flow rate.

Figure 5:
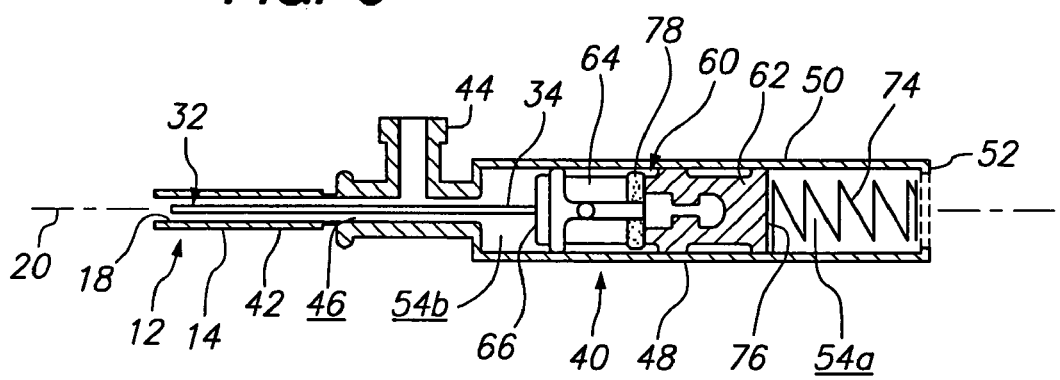
FIG. 5 is a cross-sectional side view of the hub subassembly of FIG. 4, including a piston and spring therein and connected to inner and outer members of the apparatus.

As best seen in FIG. 5, the piston 60 may be slidably received in the cylinder 48, thereby dividing the chamber 54 into a proximal chamber 54a and a distal chamber 54b. The piston 60 may include one or more seals 62 for providing a fluid-tight seal between the piston 60 and the side wall 50 of the cylinder 48, while accommodating the piston 60 sliding within the chamber 54. In a preferred embodiment, the piston 60 includes a distal plunger section 64 and a proximal seal section 62 attached to the plunger section 64, as best seen in FIG. 5. The seal section 62 may be formed from semi-rigid rubber or other material that may provide a fluid-tight seal with the outer wall 50 of the cylinder 48. The plunger section 64 may be formed from plastic, metal, composite, or other material. Exemplary devices that may used for the plunger and seal sections 64, 62 include syringe plunger and piston parts sold by Merit Medical, and identified by catalog part number MSS011.

The seal section 62 may be attached to the plunger section 64, e.g., by a cooperating stem/pocket, an adhesive, an interference fit, mating threads, and the like. Thus, the plunger section 64 of the piston 50 may include a distal surface 66 that is exposed to fluid pressure within the distal chamber 54b, and consequently to fluid pressure within the interior 46 of the housing 40 and/or within the lumen 18 of the outer member 12.

Figure 6:
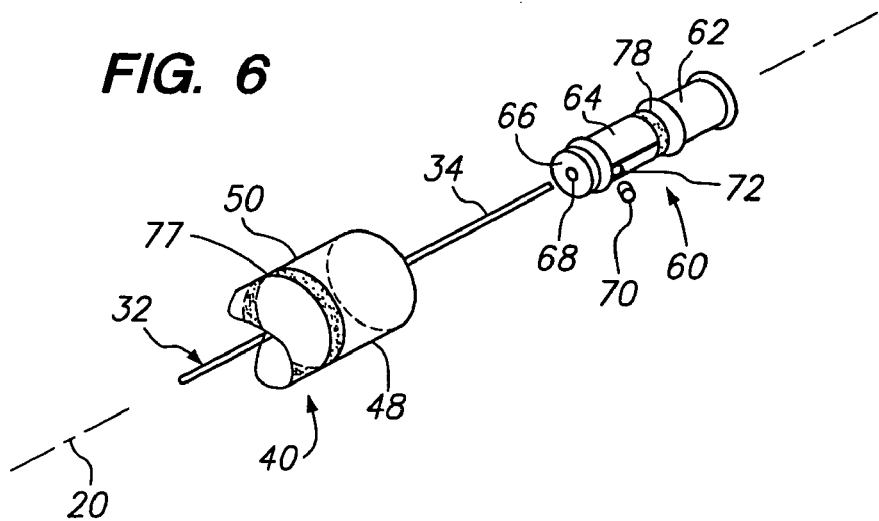
FIG. 6 is a perspective detail, showing a piston being attached to an inner member and received in a housing to provide the hub subassembly shown in FIGS. 4 and 5.

The proximal end 34 of the inner member 32 may be coupled to the piston 60, thereby coupling axial movement of the inner member 32 to axial movement of the piston 60, as shown in FIG. 5. For example, as shown in FIG. 6, the distal surface 66 of the piston 50 may include an aperture 68 through which the proximal end 34 of the inner member 32 may be received. Once the inner member 12 is inserted a desired distance into the aperture 68, the inner member 12 may be secured to the piston 60. For example, a set screw 70 may be threaded into a mating pocket 72 that may engage the proximal end 34 of the inner member 32 within the aperture 68. In addition or alternatively, the proximal end 34 of the inner member 32 may be attached to the piston 60, e.g., using an adhesive, sonic welding, crimping, an interference fit, and the like.

To provide a biasing force, a compression spring or other mechanism 74 may be provided in the proximal chamber 54a of the housing 40, e.g., for biasing the piston 60 away from the end wall 52, i.e., towards the adapter end 42 of the housing 40. The spring 74 may apply an axial force against a proximal surface 76 of the piston 60 and the end wall 52 of the cylinder 48.

For example, during assembly, the cylinder 48 may be open (i.e., may not include end wall 52 initially), and the piston 60, after being attached to the inner member 32, may be inserted into the chamber 54. The spring 74 may then be inserted into the cylinder 48, i.e., into the proximal chamber 54a, until it abuts the proximal surface 76 of the piston 60. An end cap or other end wall 52 may then be attached to the cylinder 48, e.g., using an adhesive, an interference fit, mating threads, and the like, to retain the spring 74 within the proximal chamber 54a. In one embodiment, the end wall 52 may be an annular shaped cap, although alternatively, the end wall 52 may be a solid walled cap that substantially seals the proximal chamber 54a.

The spring constant of the spring 74 may be selected to provide a desired biasing force. For example, the cylinder 48 and the piston 60 may include markers 77, 78 thereon that may become aligned with one another when the piston 60 moves to an axial location, e.g., the proximal position shown in FIGS. 2B and 7C. The axial location may correspond to a predetermined pressure within the distal chamber 54b, e.g., between about twenty and forty pounds per square inch (20-40 psi), and preferably at least about thirty pounds per square inch (30 psi).

As shown in FIGS. 4-6, the outer wall 50 of the cylinder 48 may include an annular band or other marker 77 and the piston 60 may include another annular band or marker 78. As the piston 60 retracts within the cylinder 48 (e.g., as fluid is introduced into the distal chamber 54b), the marker 78 may pass behind the marker 77, thereby indicating that a predetermined pressure has been attained within the distal chamber 54b). The marker 77 may be substantially opaque such that the marker 78 disappears to provide a visual indication. Alternatively, the marker 77 on the cylinder 48 may be transparent or translucent, and a color of the marker 78 may combine with a color of the marker 77 to provide a visual indication that the predetermined pressure has been reached. The predetermined pressure may correspond to a desired maximum pressure for the balloon 80, e.g., to ensure that the balloon 80 is expanded to a desired diameter and/or to prevent risk of the balloon 80 rupturing.

In an alternative embodiment, the proximal chamber 46a of the cylinder 48 may be filled with a compressible fluid, e.g., nitrogen, carbon dioxide, or air, that may be pressurized to a predetermined pressure to bias the piston 50 away from the end wall 44. As fluid is introduced into the distal chamber 46b, the pressure of the fluid may exceed the predetermined pressure, thereby causing the piston 60 to move proximally and compressing the fluid within the proximal chamber 46a until the pressures within the chambers 46a, 46b are substantially equal to one another. In another alternative embodiment, an extension spring (not shown) may be provided in the distal chamber 54b that may be coupled to the piston 60 and the cylinder 48 at the end near the side port 44 to bias the piston 60 distally.

Alternatively, the hub subassembly 38 may not include a biasing mechanism, e.g., no spring 74 or compressible fluid. Instead, movement of the piston 60 may be controlled directly by pressure and/or vacuum applied to inflate and/or deflate the balloon 80, respectively. For example, when a substantially incompressible fluid is delivered into the lumen 18 of the outer member 12, the pressure differential between the piston 60 and the balloon 80 may initially cause the piston 60 to slide proximally, thereby applying a proximal tensional load to the inner member 32 while the balloon 80 is expanding. When a negative pressure (vacuum) is applied to evacuate the fluid from the lumen 18 and deflate the balloon 80, the negative pressure differential between the piston 60 and the balloon 80 may initially cause the piston 60 to slide distally, thereby applying a distal compressive load to the inner member 32 while the balloon 80 is, deflating.

A desired pressure differential may be achieved by using a viscous fluid (i.e., a fluid more viscous than air) and/or by creating a restriction (not shown) within the lumen 18 distal to the side port 44 to delay the pressure from entering or exiting the balloon 80. This pressure differential may be particularly important when inflating and/or deflating an everted balloon. In addition, or alternatively, a constriction may be provided within the lumen 18, e.g., between the side port 44 and the distal end 16 to cause the piston 60 to move before fluid is introduced into the balloon 80.

Figure 8:
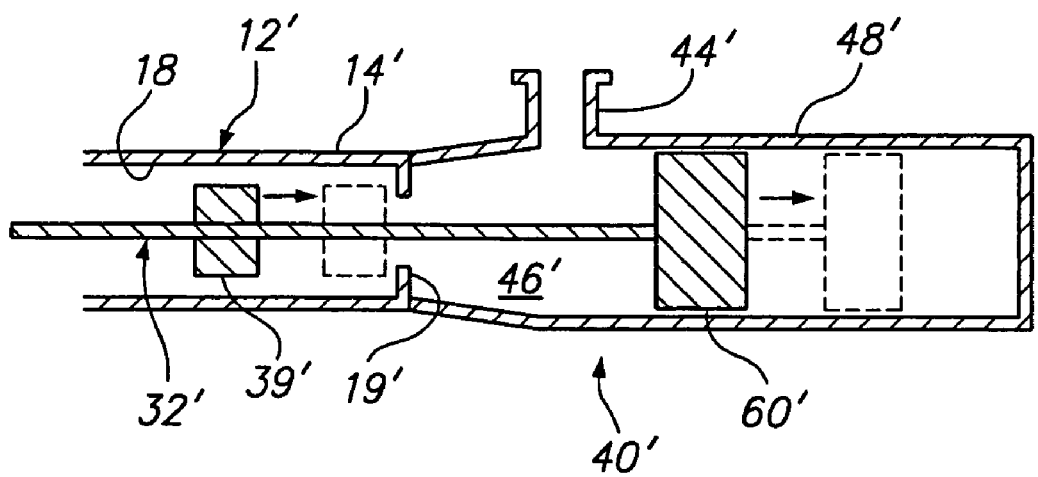
FIG. 8 is a cross-sectional detail of an alternative embodiment, showing cooperating stops for preventing over-inflation of the apparatus.

Optionally, as shown in FIG. 8, cooperating stops 19,' 39' may be provided for preventing over-inflation of the balloon 80 (not shown in FIG. 8). For example, a cylindrical stop 39' may be provided on the inner member 32' and an annular stop 19' may be provided that extends into the lumen 18' of the outer member 12' (or alternatively into the interior 46' of the housing 40' distal to the side port 44'). Preferably, the inner diameter or cross-section of the stop 19' is less than the diameter or cross-section of the stop 39' such that the stops 19,' 39' limit relative motion of the inner member 32' and/or seals the lumen 18' from further inflation.

When the inner member 32' is in a distal position, fluid may flow freely through the lumen 18' around the stop 39 to inflate the balloon 80, causing the inner member 32' and the stop 39' to move proximally, as explained above. When the inner member 32' moves to a proximal position (shown in phantom), the stop 39' may engage the stop 19' on the outer member 12.' Preferably, the proximal position corresponds to a maximum fluid pressure desired for inflating the balloon 80, thereby preventing the balloon from being over-inflated, which may risk rupturing or otherwise damaging the balloon 80.

Turning to FIGS. 1-3B, the balloon 80 is carried on the distal end 16 of the outer member 12. Generally, the balloon 80 may be expandable from a collapsed state (shown in FIGS. 2A and 3A) to an expanded state (shown in FIGS. 2B and 3B) when an inflation medium (not shown) is introduced into an interior 82 of the balloon 80. In an alternative embodiment, other expandable members, e.g., a mechanically expandable or self-expanding member (not shown) may be provided instead of the balloon 80.

The balloon 80 may be formed from a flexible, substantially inelastic material, e.g., a nonelastomeric material, such as PET, nylon, polyethylene, polyurethane, PEBAX, and the like, that may provide a substantially noncompliant balloon 80 that may expand to a predetermined size once a minimum pressure is introduced into the interior 82. In this embodiment, the size of the balloon 80 in the expanded state may be fixed. Alternatively, the balloon 80 may be formed from an elastic material, such that the size of the balloon 80 in the expanded state is dependent upon the pressure or volume of fluid delivered within the interior 82, as is known in the art.

In a preferred embodiment, the balloon 80 includes a proximal end 84, a distal end 86, and an expandable intermediate section 88 defining the interior 82 of the balloon 80. The proximal end 84 of the balloon 80 may be attached to the distal end 16 of the outer member 12, and the distal end 86 of the balloon 80 may be attached to the distal end 36 of the inner member 32. When the proximal end 84 of the balloon 80 is attached to the outer member 12, the interior 82 of the balloon 80 may communicate with the lumen 18 of the outer member 12. Alternatively, the proximal end 84 of the balloon 80 may extend proximally, replacing all or a portion of the outer member 12 (not shown). In a further alternative, the proximal end 84 of the balloon 80 may be laminated or drawn over a stiffer proximal shaft (not shown), or may be supported by an outer sleeve 70.

Preferably, as best seen in FIGS. 3A and 3B, the proximal end 84 of the balloon 80 may overlie and be attached to the distal end 16 of the outer member 12, e.g., using an adhesive, sonic welding, crimping, a compressive sleeve, an interference fit, and the like. The distal end 36 of the inner member 32 may extend through the interior 82 of the balloon 80 (i.e., through the intermediate section 88), and at least partially into the distal end 86 of the balloon 80, optionally extending an entire length of the distal end 86 of the balloon 80. Similar to the proximal end 84, the distal end 86 of the balloon 80 may be attached to the distal end 36 of the inner member 32, e.g., using an adhesive, sonic welding, crimping, a compressive sleeve, an interference fit, and the like. In a preferred embodiment, a band of material, e.g., polyamide, may be attached or otherwise provided over the proximal and distal ends 84, 86 of the balloon 80 to attach the ends 84, 86 to the outer and inner members 12, 32.

The distal end 86 of the balloon 80 may extend beyond the distal end 36 of the inner member 32, e.g., to provide a floppy or otherwise substantially atraumatic tip for the apparatus 10. For example, the distal end 86 of the balloon 80 may have a length of at least about fifty millimeters (50 mm), and the distal end 36 of the inner member 32 may only extend about twenty millimeters (20 mm) or less into the distal end 86 of the balloon 80. Alternatively, the distal end 36 of the inner member 32 may extend beyond the distal end 86 of the balloon 80, and may terminate in a substantially atraumatic tip (not shown).

In the collapsed state, shown in FIGS. 2A and 3A, the balloon 80 may conform substantially to the diameter of the outer member 12. Preferably, the proximal and distal ends 84, 86 of the balloon 80 and the distance between the distal ends 16, 36 of the outer and inner members 12, 32 are such that the balloon 80 is under slight axial tension in the collapsed state, thereby minimizing risk of the balloon 80 expanding, kinking, otherwise increasing in cross-section and/or catching on anything contacted by the balloon 80.

The balloon 80 is expanded to the expanded state, shown in FIGS. 2B and 3B, by introducing an inflation medium (not shown) into the lumen 18 of the outer member 12, and consequently into the interior 82 of the balloon 80. As explained above, when an inflation medium is introduced into the lumen 18, fluid initially enters the interior 46 of the housing 40 (not shown, see FIGS. 4 and 5), and consequently into the distal chamber 54b of the cylinder 48 (also not shown, see FIGS. 4 and 5). As the fluid pressure within the distal chamber 54b exceeds the bias of the spring 74 (or other biasing mechanism), the piston 60 may move proximally within the cylinder 48, thereby pulling the inner member 32 proximally.

As best seen in FIGS. 3A and 3B, proximal movement of the inner member 32 relative to the outer member 12 causes the distal end 86 of the balloon 80 to move towards the proximal end 84 of the balloon 80. Thus, in the collapsed state, the intermediate section 88 of the balloon 80 may have a length $L_C$, while, in the expanded state, the intermediate section 88 may have a length $L_E$ that is substantially shorter than $L_C$. Preferably, in the expanded state, the balloon 80 may have a diameter between about four and ten millimeters (4-10 mm), and a length $L_E$ between about two and ten millimeters (2-10 mm). For example, in an exemplary embodiment, the balloon may have a diameter of about six millimeters (6 mm) at thirty pounds per square inch (30 psi) internal pressure and a length $L_E$ between about four and eight millimeters (4-8 mm).

In a preferred embodiment, the balloon 80 at least partially everts in the expanded state, i.e., the length $L_E$ of the balloon 80 may be substantially smaller than the diameter. Stated differently, in the expanded state, the proximal and distal ends 84, 86 of the balloon 80 may become sufficiently close to one another that they at least partially enter the interior 82 of the balloon 80, as shown in FIG. 3B, thereby defining a toroidal shape. This everted configuration may facilitate creating hemostasis within a puncture in a wall of a body lumen (not shown) while allowing at least some fluid flow to continue along the body lumen, as explained further below.

With reference to FIGS. 3A, 3B, and 5, in a preferred embodiment, the cross-section of the distal chamber 54b of the cylinder 48 may be substantially larger than a cross-section of the lumen 18 of the outer member 12. For example, the cylinder 48 may have an inner diameter between about 0.050-0.100 inch (1.25-2.5 mm), while the lumen 18 may have a diameter between about 0.010-0.020 inch (0.25-0.50 mm). Thus, a cross-sectional area of the distal surface 66 of the piston 60 may be substantially greater than a cross-sectional area of the lumen 18.

When a fluid is introduced into the side port 44 of the hub subassembly 38 under pressure, the pressure may impose a proximal force on the distal surface 66 of the piston 60. Because of the relatively large area of the distal chamber 54b, fluid may flow easily into the distal chamber 54b before flowing down the lumen 18 into the interior of the balloon 80. Thus, as fluid is introduced into the side port 44, a proximal force may be applied to the piston 60 before or as the balloon begins to expand, thereby shortening the balloon 80 before or as it expands towards the expanded state.

Conversely, if fluid is evacuated out of the side port 44, the fluid from the distal chamber 54b of the cylinder 48 may be removed before fluid is drawn up the lumen 18 and the balloon 80 begins to collapse. The resulting vacuum may pull the piston 60 distally, causing the balloon 80 to elongate towards its collapsed length $L_C$ before or as the balloon collapses towards the collapsed state. This feature may be particularly useful for ensuring that the balloon 80 is collapsed to as small a profile as possible when the balloon 80 is collapsed from the expanded state to the collapsed state, as explained further below.

Optionally, as shown in FIGS. 7A-7F, the apparatus 10 may include other components, e.g., to provide a kit for performing a procedure on a patient. For example, an introducer sheath 110 may be provided that includes a proximal end 112, a distal end 114, and a lumen 116 extending therebetween. The introducer sheath 110 may include a tapered distal tip 117, e.g., for facilitating advancing the introducer sheath 110 through a puncture, as is well known to those skilled in the art.

In addition, the introducer sheath 110 may include a side port 120 on the proximal end 114 communicating with the lumen 116 and/or may include one or more seals (not shown), e.g., to prevent substantial proximal flow of fluid through the lumen 116, as is known in the art. As shown in FIG. 7E, a source of sealing compound 130 may be connectable to the side port 120, e.g., for delivering a sealing compound into the lumen 116 of the introducer sheath 110.

With continued reference to FIG. 7E, a dual syringe assembly 130 may be provided that includes two components of a sealing compound. In a preferred embodiment, a prepolymer is provided in each syringe 132 of the syringe assembly 130. A "Y" fitting 140 may be provided that includes proximal sections 142 that communicate with a single distal section 144. The proximal and distal sections 142, 144 may include connectors, e.g., luer lock connectors and the like (not shown), for connecting with outlets 136 of the syringes 132 and with the side port 120 of the introducer sheath 110. Thus, the "Y" fitting 140 may be connectable to outlets 136 of the syringes 132 such that the components ejected out of the syringes 132 may mix before being injected into the side port 120 of the introducer sheath 110. The "Y" fitting 140 may include one or more components, e.g., separate lengths of tubing and the like (not shown), as will be appreciated by those skilled in the art.

In a preferred embodiment, the components are prepolymer that mix to create a hydrogel, as explained further below. Additional information on hydrogels and systems for injecting them are disclosed in U.S. Pat. Nos. 6,152,943, 6,165,201, 6,179,862, 6,514,534, and 6,379,373, and in co-pending application Ser. Nos. 09/776,120 filed Feb. 2, 2001, 10/010,715 filed Nov. 9, 2001, and 10/068,807 filed Feb. 5, 2002. The disclosures of these references and any others cited therein are expressly incorporated by reference herein.

In addition, the kit may include a syringe 160 (as shown in FIGS. 7C and 7F) or other device for delivering inflation medium into the side port 44 of the apparatus 10, as explained above. Optionally, the kit may also include a stylet or obturator (not shown) that may be inserted into the lumen 116 of the introducer sheath 110, e.g., to facilitate percutaneously inserting the introducer sheath 110 through tissue, as is known to those skilled in the art. In addition or alternatively, one or more guidewires (not shown) may also be provided.

Turning to FIGS. 7A-7F, a method for sealing a passage through tissue is shown. Preferably, the passage is a percutaneous puncture 190 extending from a patient's skin 192 to a blood vessel or other body lumen 194. For example, the vessel 194 may be a peripheral artery, e.g., a femoral artery, a carotid artery, and the like.

Figure 7A:
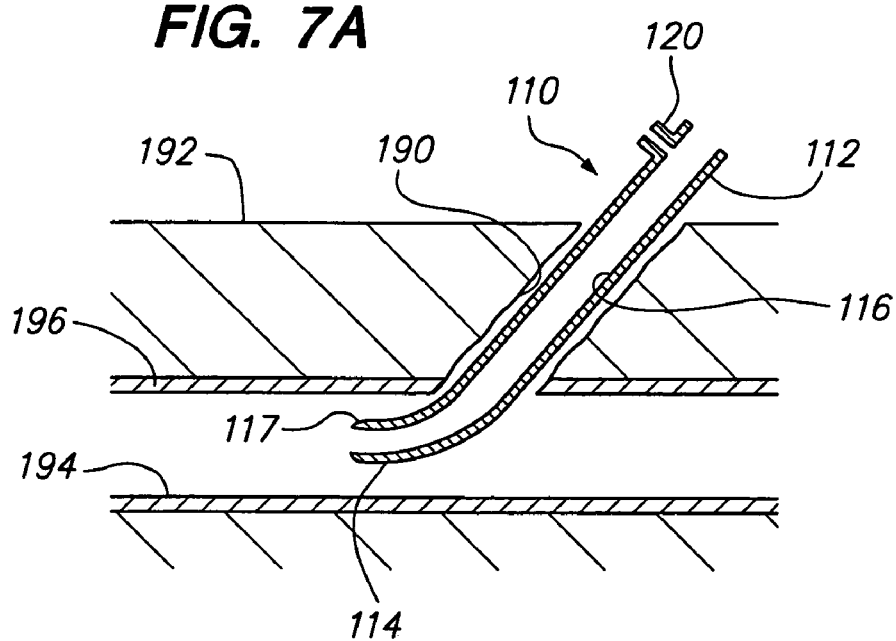
FIGS. 7A-7F are cross-sectional views of a percutaneous puncture communicating with a blood vessel showing a method for sealing the puncture, in accordance with the present invention.

Initially, as shown in FIG. 7A, an introducer sheath 110 may be placed within the puncture 190 such that the distal end 114 is disposed within the vessel 192. For example, a stylet having a sharpened distal tip (not shown) may be inserted through the lumen 116 of the introducer sheath 110 such that the sharpened distal tip extends beyond the distal end 116 of the introducer sheath 110. The introducer sheath 110 and stylet may then be inserted directly through the patient's skin 192 until the distal end 114 is disposed within the vessel 194. Alternatively, the introducer sheath 112 may be advanced over a guidewire previously inserted through the puncture 190 into the vessel 194, using known procedures, such as those described in the Background above.

One or more instruments (not shown) may be advanced through the introducer sheath 110 and into the vessel 194, e.g., to perform a diagnostic and/or therapeutic procedure within the patient's body. The one or more instruments may include catheters, e.g., balloon catheters, stent delivery catheters, imaging catheters, and the like, guidewires, and/or other devices. Upon completing the procedure(s), any instruments may be removed and the puncture 190 may be sealed using an apparatus, such that shown in FIGS. 1-6 and described above.

Figure 7B:
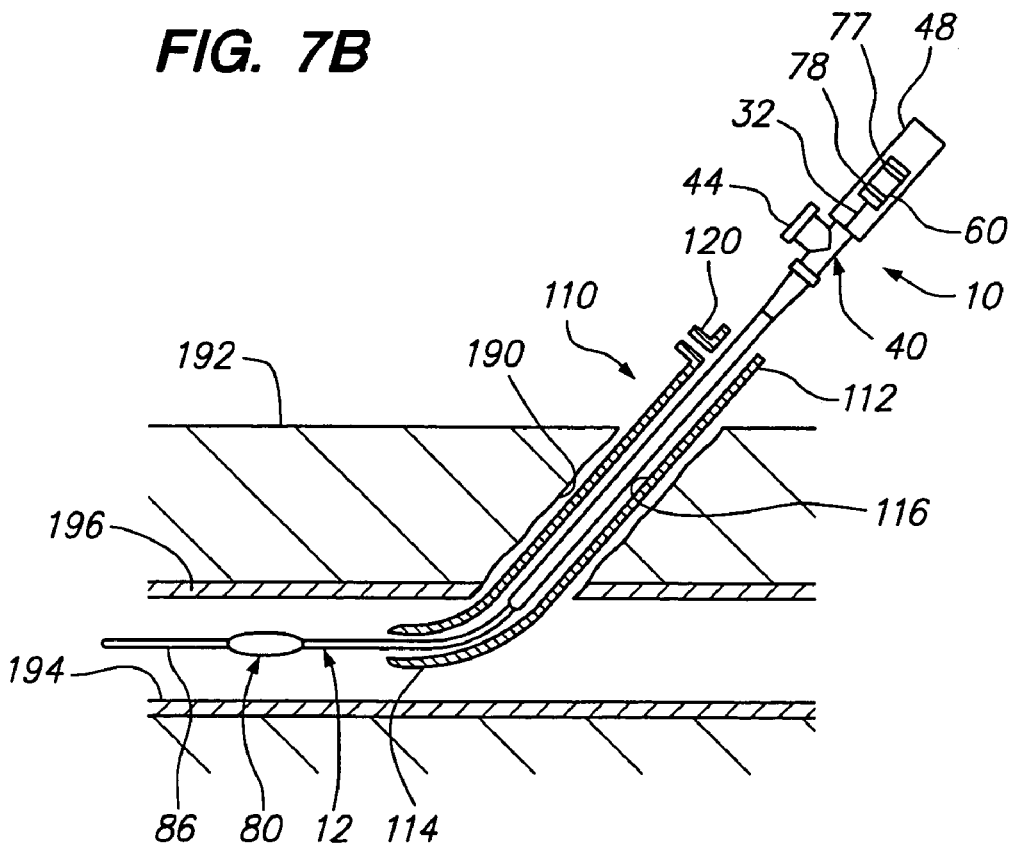
Figure 7C:
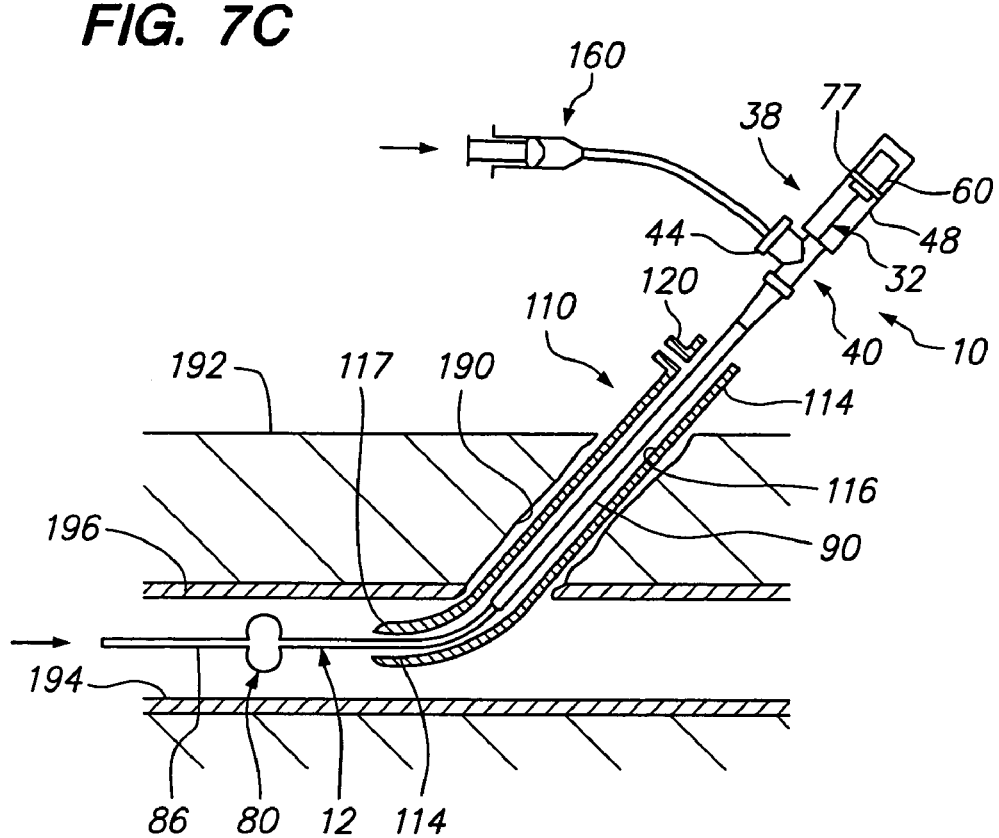

Turning to FIG. 7B, with the balloon 80 in the collapsed state, the apparatus 10 may be inserted through the lumen 116 of the introducer sheath 110 until the balloon 80 is disposed within the vessel 194. Optionally, the apparatus 10 may include one or more markers, e.g., radiopaque markers (not shown), to facilitate monitoring insertion of the apparatus 10 using external imaging, e.g., fluoroscopy, ultrasound, magnetic resonance imaging ("MRI"), and the like.

Alternatively or in addition, one or more visual markers (not shown) may be provided, e.g., on the proximal end 14 of the outer member 12 (or the outer sleeve 90 if provided around the outer member 12). The markers may include one or more colored bands at predetermined locations along a length of the outer member 12 relative to the balloon 80. For example, a distance between a band on the proximal end 14 of the outer member 12 may correspond to a length of the introducer sheath 110, thereby providing a visual indication when the apparatus 10 has been advanced sufficiently to expose the balloon 80 beyond the distal end 114 of the introducer sheath.

As shown in FIG. 7C, once the balloon 80 is disposed within the vessel 194, the balloon 80 may be expanded to the expanded state, e.g., by introducing fluid into the side port 44 from a syringe 160 through the outer member 12 and into the balloon 80. As explained above, as fluid is introduced into the side port 44, the inner member 32 may be moved proximally relative to the outer member 12, thereby causing the balloon 80 to shorten as it expands. Preferably, the fluid is introduced until the piston 60 moves proximally and the markers 77, 78 are aligned with one another, as shown in FIG. 7C. This may inform the user that a desired pressure has been reached and/or that the balloon 80 has been expanded to a desired size.

If the apparatus 10 includes a detachable outer sleeve 90, the rest of the apparatus 10, i.e., the outer and inner members 12, 32, balloon 80, and hub subassembly 38, may be removed, if desired. For example, if the balloon 80 accidentally ruptures, the outer sleeve 90 may be disconnected, and the apparatus 10 replaced with another one having an intact balloon (not shown). In addition or alternatively, if it is discovered that the balloon 80 is the wrong size for the given anatomy (e.g., is too small for the puncture 190 or too large for the vessel 194), the apparatus 10 may be replaced with one having a larger or smaller balloon.

Figure 7D:
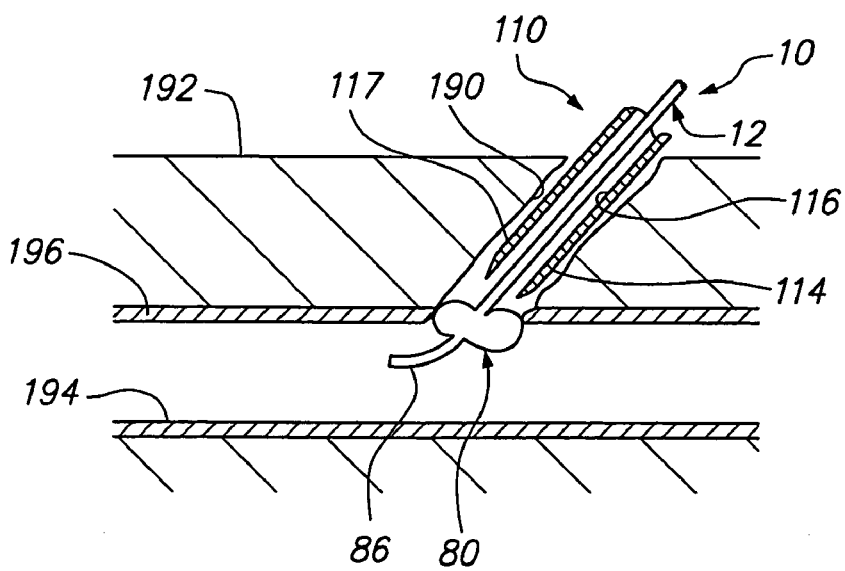
Figure 7E:
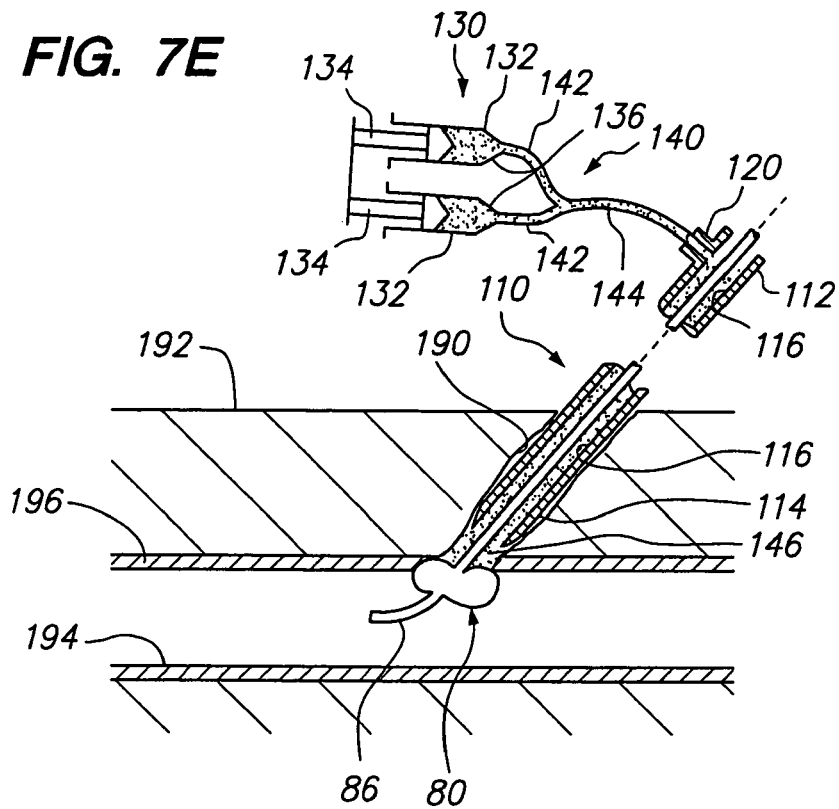
Figure 7F:
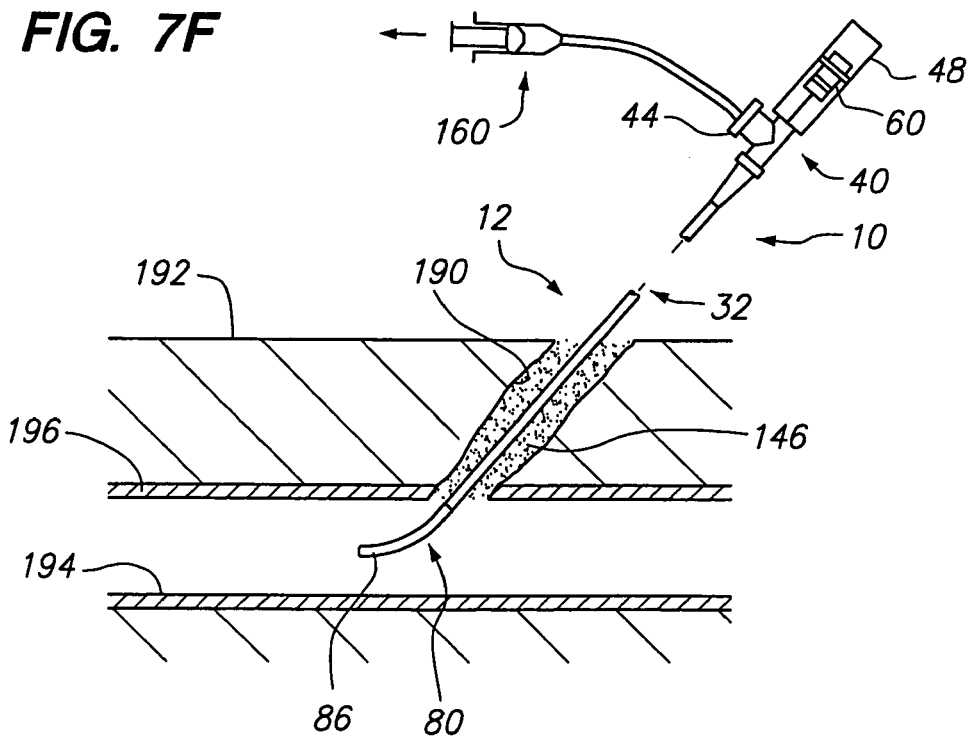

Turning to FIG. 7D (which omits the proximal components of the apparatus 10 merely for simplicity), the apparatus 10 may be partially withdrawn from the puncture 190 with the balloon 80 in the expanded state, i.e., until the balloon 80 engages the puncture 190. Preferably, the balloon 80 substantially seals the puncture 190, i.e., substantially isolating the puncture 190 from the interior of the vessel 194. Thus, the apparatus 10 may provide temporary hemostasis, e.g., preventing blood from passing through the puncture 190. Thus, even without the additional steps that follow, the apparatus 10 may be used to provide hemostasis in emergency situations in order to minimize loss of blood until a puncture victim may be treated.

In preferred embodiment, the balloon 80 at least partially everts in the expanded state, as described above. This everted configuration may be particularly for providing hemostasis, while still allowing blood flow to continue along the vessel 194. For example, as shown in FIG. 7D, the diameter of the balloon 80 may be substantially greater than its length in the expanded state. Thus, when the balloon 80 is pulled into engagement with the wall 196 of the vessel 194, at least a portion of the vessel 194 lumen may remain unobstructed, as shown.

Figure 9:
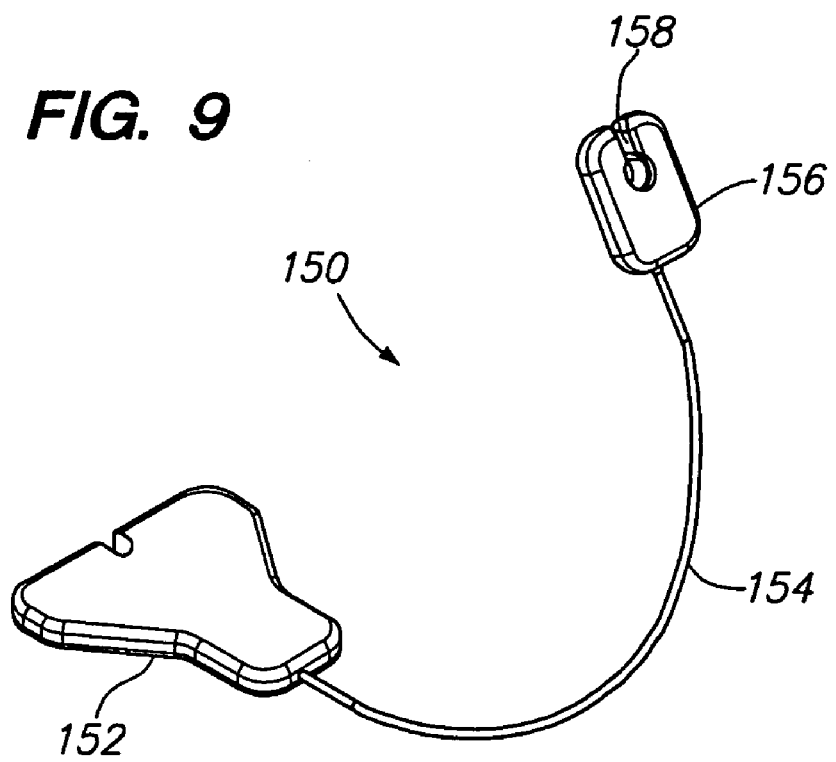
FIG. 9 is a perspective view of a tensioner, in accordance with the present invention.

Optionally, in order to maintain the balloon 80 substantially against the puncture 190 without requiring an individual to hold the apparatus 10, a tensioner 150 may be provided that may apply a proximal force to the apparatus 10 to maintain the balloon 80 substantially against the puncture 190. For example, as shown in FIG. 9, the tensioner 150 may include a base portion 152, a biasing support 154, and a saddle 156. The base portion 152 may be substantially flat or shaped to conform to the patient's anatomy, e.g., to follow the contour or otherwise lie on a patient's leg (not shown) or other skin 192 overlying the puncture 190.

The saddle 156 may include a wire or plate including a slot 158 or other mechanism for grasping or otherwise engaging the apparatus 10. For example, the slot 158 may have a width large enough to receive the outer member 12 or the outer sleeve 90 therein but smaller than the hub subassembly 38. The biasing support 154 includes ends connected to the base support 152 and the saddle 156 and may be biased to provide a predetermined spacing between the base support 152 and the saddle 156. Preferably, the biasing support 154 is adjustable to allow the spacing between the base support 152 and saddle 156 to be adjusted based upon the particular anatomy encountered during a procedure.

Alternatively, the tensioner 150 may simply be a wire frame (not shown) that is bent or otherwise shaped to provide the base support 152, biasing support 154, and saddle 156. It will be appreciated that other structures, including two or more separate parts may be assembled to provide a tensioner in accordance with the present invention. For example, in a further alternative, the tensioner may be made from a single structure formed, molded, or otherwise created in a desired shape.

During use, the base portion 152 may be placed in contact with the patient, e.g., set on the patient's skin 192 adjacent to the puncture 190. The apparatus 10 may be received in the saddle 156, e.g., by inserting the outer member 12 into the slot 158. The apparatus 10 may then be released, and the tensioner 150 may pull the apparatus 10 proximally with sufficient tension to maintain the balloon 80 in contact with the wall 196 of the vessel 194. If necessary, the biasing support 154 may be reshaped to increase or decrease the distance between the saddle 156 and the base support 152 and/or to increase or decrease the tension as necessary for the anatomy encountered. Thus, the tension imposed by the tensioner 150 may apply a desired tensile force to the balloon to maintain hemostasis while preventing the balloon 80 from being pulled into the puncture 190 and/or preventing the wall 196 of the vessel 194 from excessive tenting.

Alternatively, the saddle 156 of the tensioner 150 may be engaged in one of a plurality of mating slots (not shown) provided in the outer wall 50 of the cylinder 48 to provide a desired tension on the balloon 80. Thus, the slots may allow a desired tension independent of a patient profile (e.g., obese or thin) where a distance of the vessel 194 from the skin 192 varies from shallow to deep.

Turning to FIG. 7E, a sealing compound 146 may be delivered into the puncture. Preferably, the sealing compound is a liquid or other flowable material that may be injected into the puncture 190. Because of the hemostasis provided by the balloon 80, the sealing compound 146 may be delivered without substantial concern that the sealing compound 146 may leak into the vessel 194.

More preferably, the sealing compound includes multiple component prepolymers that create a hydrogel when mixed together, as described above. Such a sealing compound may be particularly useful, because it may be substantially harmless to the patient even if it somehow leaks into the vessel 194. Unlike collagen or other hemostasis-promoting materials, which may cause thrombosis and/or embolism when exposed to blood within a vessel, hydrogel prepolymers may not promote hemostasis within a blood vessel. In fact, such prepolymers, if leaked into a vessel, may simply dilute and flow away, where they may be metabolized naturally without substantial risk of creating thrombus. This is another reason why it may be useful to seal the puncture 190 with an everted balloon 80, while still allowing fluid to continue to flow along the vessel 194, as described above. In case the hydrogel leaks into the vessel 194 around the balloon 80, blood flow may dilute and carry the hydrogel away, where it may be safely metabolized naturally, e.g., by the liver.

As shown in FIG. 7E, a two-part sealing compound is shown contained within a dual syringe assembly 130. The prepolymers or other components in the syringes 132 may be mixed or otherwise prepared using known procedures. The plungers 134 of the syringes 132 may be linked such that they may be depressed substantially simultaneously, thereby delivering the prepolymers simultaneously. The prepolymers may mix in the "Y" fitting 140 into a liquid sealing compound 146, and then be delivered into the side port 120 of the introducer sheath 110. Alternatively, an auto injector device, including a spring, motor, pneumatic pressure, and the like (not shown) may be provided for delivering the prepolymers at a desired substantially continuous rate. Such a device may prevent unintended pauses during delivery, which may cause the "Y" fitting 140 or other passages through which the sealing compound passes from becoming obstructed.

The liquid sealing compound 146 may be injected through the lumen 116 of the introducer sheath 110 out the distal end 114 into the puncture 190. The introducer sheath 110 may remain stationary as the sealing compound 146 is delivered, thereby allowing the sealing compound to flow into the puncture 190 around the introducer sheath 110. In this method, a sealing element (not shown) may be provided on the exterior of the introducer sheath 110 for sealing the puncture 190 at or near the surface of the skin 192. For example, a balloon or other expandable member (not shown) may be provided on or near the proximal end 112 of the introducer sheath 110. The expandable member may be expanded to substantially seal the proximal end of the puncture 190, thereby preventing substantial amounts of sealing compound leaking out of the puncture. Alternatively, a "C" shaped clip or other element (not shown) may be attached around the introducer sheath 110, e.g., at the skin 192 for substantially sealing the puncture 190.

Alternatively, the introducer sheath 110 may be withdrawn proximally from the puncture 190 as the sealing compound 146 is delivered, thereby filling the puncture tract with the sealing compound 146, as shown in FIG. 7F. In the latter case, an annular ridge, bump, or other element (not shown) may be provided on an exterior of the proximal end 14 of the outer member 12 (or the outer sleeve 90) to prevent the sealing compound from being pulled proximally along with the introducer sheath 110. In addition or alternatively, the lumen 116 of the introducer sheath may be coated with a lubricious material, e.g., silicone to facilitate the introducer sheath 110 sliding over the sealing compound 146.

In a further alternative, a balloon, braid structure, and/or other expandable member (not shown) may be provided on the distal end 114 of introducer sheath 110. This expandable member may be expanded and deflated (one or more times) to dilate or otherwise enlarged the puncture 194 tract to accommodate more sealing compound 146 being delivered into the puncture 190. Alternatively, the expandable member may remain expanded while the introducer sheath 110 is at least partially withdrawn from the puncture 190 to enlarge the puncture along its length. In another alternative, a plurality of spaced-apart balloons or other expandable members (not shown) may be provided along the introducer sheath 110 for isolating segments of the puncture 190. The introducer sheath 110 may include one or more outlets (also not shown) disposed between the balloons that communicate with the lumen 116 of the introducer sheath 110. Thus, sealing compound may be delivered into each of the individual isolated segments of the puncture 190, which may ensure sealing along the length of the puncture 190.

In an alternative embodiment, a port (not shown) may be provided in the outer sleeve 90 (not shown in FIGS. 7E and 7F), and the introducer sheath 110 may be removed before the sealing compound is delivered. The sealing compound may be delivered into the side port of the outer sleeve 90, through the lumen of the outer sleeve 90 along the outer member 12, and into the puncture 19. This alternative may reduce a volume of sealing compound necessary to fill the puncture 190 as compared to filling the volume of the lumen of a relatively large bore introducer sheath 110, as will be appreciated by those skilled in the art.

It will be appreciated that other devices may be used for delivering sealing material into the puncture 190. For example, other apparatus for delivering liquid sealing compounds, including single or multiple lumens (not shown), may be advanced over the apparatus 10, e.g., through the introducer sheath 110. Alternatively, the introducer sheath 110 may be removed, before such delivery apparatus are advanced over the apparatus 10 into the puncture 190. In a further alternative, solid plugs, such as those disclosed in U.S. Pat. No. 5,108,421 may be advanced into the puncture 190 adjacent or around the apparatus 10. Thus, the balloon 80 may provide hemostasis and/or prevent a plug or other solid or liquid sealing compound from entering the vessel 194 as it is introduced into the puncture 190.

Turning to FIG. 7F, once sufficient sealing compound 146 is delivered, the sealing compound 146 may given sufficient time to at least partially (or fully) solidify, e.g., between about five and one hundred eighty (5-180) seconds. The balloon 80 may then be collapsed to the collapsed state and then withdrawn from the puncture 190.

The syringe 160 or other device (not shown) may be used to evacuate fluid via the side port 44 to collapse the balloon 80. Preferably, as explained above, fluid may be drawn initially from the cylinder 48, thereby causing the piston 60 to advance distally and push the inner member 32 distally to elongate the balloon 80. Thus, as the balloon 80 is deflated, it may advance away from the puncture 190 to its collapsed profile, thereby avoiding contact with the sealing compound 146 as it collapses. Once fluid is removed, the piston 60 and inner member 32 may subject the balloon 80 to axial tension, thereby minimizing its profile in the collapsed state, which may facilitate removing the balloon 80 through the puncture 190 without substantially disturbing the surrounding sealing compound 146.

To facilitate removing the balloon 80, a lubricious coating (not shown) may be provided on the exterior of the outer member 12, e.g., Dow 360 silicone fluid. Such a coating may prevent the sealing compound 146 from sticking to or otherwise pulling on the outer member 12 (or the outer sleeve 90) as the apparatus 10 is withdrawn.

Optionally, external pressure may be applied, e.g., by pressing manually against the skin 192 overlying the vessel 194, e.g., to at least partially suppress flow through the vessel 194. The balloon 80 (and the rest of the apparatus 10) may be removed, and the external pressure may be maintained for sufficient time to allow the sealing compound 146 to solidify further, e.g., between about ten and one hundred eighty (10-180) seconds. The sealing compound may expand, e.g., due to its elasticity and/or due to further solidification, thereby substantially sealing the relatively small tract remaining upon removing the apparatus 10.

Alternatively, the tensioner 150 (not shown, see FIG. 9) may be used to maintain tension on the balloon 80 for a prolonged period of time with the balloon 80 providing temporary hemostasis to allow the hydrogel to cure fully in the puncture 190 before removing the apparatus 10.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for sealing a puncture extending through tissue, comprising:
   an outer member comprising proximal and distal ends defining a longitudinal axis therebetween, and a lumen extending between the proximal and distal ends;
   an expandable member comprising proximal and distal ends, the proximal end of the expandable member being coupled to the distal end of the outer member such that an interior of the expandable member communicates with the lumen, the expandable member being expandable from a collapsed state to an expanded state when fluid is introduced into the interior;
   an inner member slidably coupled to the outer member and comprising proximal and distal ends, the distal end being coupled to the distal end of the expandable member, the inner member being biased to move distally relative to the outer member for moving the distal end of the expandable member away from the proximal end of the expandable member to at least partially collapse the expandable member; and
   an element coupled to the inner member and comprising a surface exposed to the lumen such that, when fluid is introduced into the lumen, fluid pressure from the fluid pushes against the surface, causing the inner member to move proximally relative to the outer member for moving the distal end of the expandable member towards the proximal end of the expandable member a cylinder extending from the proximal end of the outer member, the element coupled to the inner member comprising a piston slidable within the cylinder and coupled to the proximal end of the inner member.

2. The apparatus of claim 1, wherein the element is configured for causing the inner member to move distally relative to the outer member for moving the distal end of the expandable member away from the proximal end of the expandable member when fluid is evacuated from the lumen.

3. The apparatus of claim 1, wherein the outer member comprises a port on the proximal end, the port communicating with the lumen for connecting a source of fluid to the lumen.

4. The apparatus of claim 1, wherein the surface comprises a distal surface of the piston.

5. The apparatus of claim 1, wherein the piston divides the cylinder into proximal and distal chambers, the distal chamber communicating with the lumen.

6. The apparatus of claim 5, further comprising a fluid within the proximal chamber, the fluid comprising a predetermined pressure for biasing the inner member distally relative to the outer member.

7. The apparatus of claim 6, wherein the fluid comprises a gas at atmospheric pressure.

8. The apparatus of claim 6, further comprising a source of fluid coupled to the port, the source of fluid configured for delivering fluid into the lumen at a pressure greater than the predetermined pressure for moving the inner member proximally relative to the outer member.

9. The apparatus of claim 1, further comprising a spring within the cylinder for biasing the inner member distally relative to the outer member.

10. The apparatus of claim 1, wherein the surface has a surface area that is substantially greater than a cross-sectional area of the lumen.

11. The apparatus of claim 1, wherein the inner member comprises a wire.

12. The apparatus of claim 1, wherein the outer member comprises a tubular member, and wherein the inner member is slidable within the outer member.

13. The apparatus of claim 12, wherein the inner member extends through the lumen of the outer member, the inner member having a cross-section smaller than a cross-section of the lumen to allow fluid to flow through the lumen around the inner member.

14. The apparatus of claim 1, wherein the expandable member comprises a balloon.

15. The apparatus of claim 1, wherein the expandable member has a length in the collapsed state, and wherein, in the expanded state, a distance between the distal ends of the inner and outer members changes to shorten the length as the expandable member expands towards the expanded state.

16. The apparatus of claim 15, wherein the length shortens such that the proximal and distal ends of the expandable member at least partially evert into the interior of the expandable member.

17. The apparatus of claim 1, wherein, in the collapsed state, the inner member is biased distally to subject the expandable member to axial tension to minimize a profile of the expandable member.

18. The apparatus of claim 1, wherein the outer member has an outer diameter of about 0.025 inch (0.625 mm) or less.

19. The apparatus of claim 1, further comprising an elongate sheath comprising proximal and distal ends, and a lumen extending therebetween, the lumen having sufficient size for receiving the outer member therein when the expandable member is in the collapsed state.

20. The apparatus of claim 19, further comprising a source of liquid sealing compound coupled to the proximal end of the sheath for delivering liquid sealing compound into the lumen between the sheath and the outer member.

21. The apparatus of claim 20, wherein the liquid sealing compound comprises a hydrogel.

* * * * *